United States Patent [19]

Nordmeyer et al.

[11] Patent Number: 4,491,011

[45] Date of Patent: Jan. 1, 1985

[54] DIALYZING INJECTION SYSTEM FOR INSTRUMENTAL DETECTION

[75] Inventors: Francis R. Nordmeyer; Lee D. Hansen, both of Orem, Utah

[73] Assignee: Brigham Young University, Provo, Utah

[21] Appl. No.: 387,357

[22] Filed: Jun. 11, 1982

[51] Int. Cl.³ .................. G01N 27/28; G01N 31/08; B01D 13/00
[52] U.S. Cl. ................... 73/61.1 C; 210/656; 73/53
[58] Field of Search ............. 210/253, 636, 644, 645, 210/656, 669, 806, 186; 422/81; 73/864.24, 61 R, 53

[56] References Cited

U.S. PATENT DOCUMENTS

| | | | |
|---|---|---|---|
| 2,879,141 | 3/1959 | Skeggs | 73/864.24 |
| 2,899,280 | 3/1957 | Whitehead et al. | 73/864.24 |
| 3,488,154 | 1/1970 | Hvonas | 422/81 |
| 3,727,612 | 4/1973 | Sayers | 210/641 |
| 3,771,658 | 10/1971 | Brumfield | 210/186 |
| 4,312,757 | 1/1982 | Brumfield | 210/644 |

FOREIGN PATENT DOCUMENTS 396819 10/1977 Sweden .

OTHER PUBLICATIONS

Elo H. Hansen & Jaromir Ruzicka, *Flow Injection Analysis, Part VI, The Determination of Phosphate and Chloride in Blood Serum by Dialysis and Sample Dilution*, 1976, Anal. Chim. Acta, 87, pp. 353-362.
R. W. Seibers, *Sequential Dialysis on the Technicon SMA 6/60 (4+2)*, N.Z.J. Med. Lab. Technol., Nov., 1977, pp. 73, 74.

*Primary Examiner*—John W. Caldwell, Sr.
*Assistant Examiner*—Ellwood G. Harding
*Attorney, Agent, or Firm*—George H. Mortimer

[57] ABSTRACT

The present invention relates to apparatus for and a method of instrumental detection. The apparatus comprises in combination (a) an instrumental detector such as a chromatographic, spectrophotometric, fluorimetric, electrometric determination detector, and the like for analyzing an analyte and (b) a hollow dialysis fiber for eliminating such materials as insoluble and soluble polymeric materials and polymer bonded portions from the sample to be detected that would foul the instrumental detector so that the material delivered to the eluent stream flowing to the instrumental detection means is essentially free of such contaminating materials. The method comprises purifying the sample to be subjected to instrumental detection by any of the detectors mentioned above in a preliminary equilibrium dialysis which strips from that portion of the sample which enters the analyte essentially all such contaminating materials, delivering the essentially polymer-free analyte to the eluent stream flowing to the instrumental detector and subjecting it to instrumental detection. The dialysis chambers may be rinsed after each cycle and the operations are preferably completely automated.

18 Claims, 3 Drawing Figures

DIALYZING INJECTION SYSTEM FOR INSTRUMENTAL DETECTION

INTRODUCTION

The present invention relates to an improvement in the art of instrumental detection. This improvement involves both an apparatus aspect and a method or process aspect.

The improved apparatus of the invention comprises in combination (a) instrumental detection means, e.g., chromatography means, spectrophotometric means, fluorimetric means, electrometric determination means, and the like, for analyzing an analyte and (b) hollow fiber dialysis means for eliminating materials which would foul the instrumental determination means, such as the chromatographic columns in chromatography means, e.g., the insoluble and soluble polymeric materials and polymer-bound portions of the sample so that the material delivered to the eluent stream of the instrumental detection means is essentially free of such contaminating materials.

The improved method comprises subjecting the sample to be subjected to instrumental detection, e.g., to chromatography, to a preliminary dialysis, preferably equilibrium dialysis, to strip from the portion of this sample that enters the analyte essentially all the soluble polymeric materials, such as the polymer-bound portion of the sample, delivering the essentially polymer-free analyte to the eluent stream and subjecting the eluent stream containing the analyte to chromatography or other instrumental detection. Auxiliary operations, such as rinsing of the dialysis chambers after each cycle, are preferably carried out.

Preferably the delivery of the dialysate to the eluent stream and the rinse of the dialyzer between samples are completely automated operations.

BACKGROUND OF THE INVENTION

The presence of soluble polymeric materials in a sample to be analyzed by chromatography, especially liquid, as opposed to gas, chromatography, often makes it difficult to carry out the liquid chromatography for a number of reasons. Among these reasons, as listed in Elo H. Hansen and Jaromir Ruzicka, FLOW INJECTION ANALYSIS, PART VI. THE DETERMINATION OF PHOSPHATE AND CHLORIDE IN BLOOD SERUM BY DIALYSIS AND SAMPLE DILUTION, ANAL. CHIM. Acta, 87, 353–363, (1976), are:

(1) Interference of proteins and other large molecules with the chromatography.

(2) The tendency of these large molecules to deposit in and foul the conduits, flow cells, etc., of the analyzer.

(3) The signal may be outside the range of the detector.

(4) The amount of sample material available may be less than the minimum amount required for analysis.

A way to reduce the amount of sample required in the use of the Technicon SMA 6/60 by apparatus changes and modified procedure is disclosed in R. W. L. Siebers, SEQUENTIAL DIALYSIS ON THE TECHNICON SMA 6/60 (4+2), N. Z., J. Med. Technol., November 1977. Hansen et al. suggest the other problems may be overcome or mitigated by subjecting the sample to dialysis or sample dilution before injection of the sample material into the capillary column, but their experiments using their equipment, in clinical chromatography, especially of blood serum, were interpreted strongly to favor sample dilution as the better solution to the problems and to avoid dialysis wherever possible.

These prior art proposed systems operate on *flow*, not on *equilibrium* as in the present invention; and while it is possible by precise timing to obtain fairly reproducible results with the prior art flow systems, the results are less satisfactory than the results obtainable by the present invention based on equilibrium of ingredients in the dialysis column and out of it as hereinafter defined. Usually the equilibrium system operates intermittently (1) to fill the dialysis column and surrounding annulus, (2) to equilibrate the liquids in the column and annulus (non-flowing), and (3) to remove the equilibrated liquids from the column and annulus. However, dialysis can be carried out in accordance with the invention by continuous flow with significantly better results, particularly a more complete transfer of dialyzable material at a given flow rate, than the prior art systems.

SUMMARY OF THE INVENTION

The problem, which the presence of soluble polymeric materials in a sample of blood serum and the like causes of making it difficult to analyze the sample by liquid chromatography and other instrumental detection, is overcome by the method of the invention by first removing the polymeric material by dialysis in a particular manner and injection of the dialysate into the chromatograph or other detection means. However, the problems with normal dialysis procedures is that they are slow, require relatively large samples, and usually result in severe dilution of the sample. The method of the invention avoids and overcomes these problems. The apparatus aspect of the invention comprises a dialyzing injection system which uses as little as 40uL of sample, means to transfer from the precisely measured sample the portion thereof that passes into the recipient liquid to form the dialysate, and means to deliver the total volume of dialysate to the eluent stream. The invention provides an attractive way to handle any samples for instrumental detection which contain undesired, unfilterable material.

The invention is useful for the analysis of ions and drugs in blood, small molecules and ions in soil and food extracts, and ions and small molecules in polymer-containing pharmaceuticals.

BRIEF DESCRIPTION OF THE DRAWINGS

The invention will be described, both as to the apparatus and method aspects, in conjunction with the drawings in which.

DETAILED DESCRIPTION OF PREFERRED EMBODIMENTS OF THE INVENTION

Figure 1:
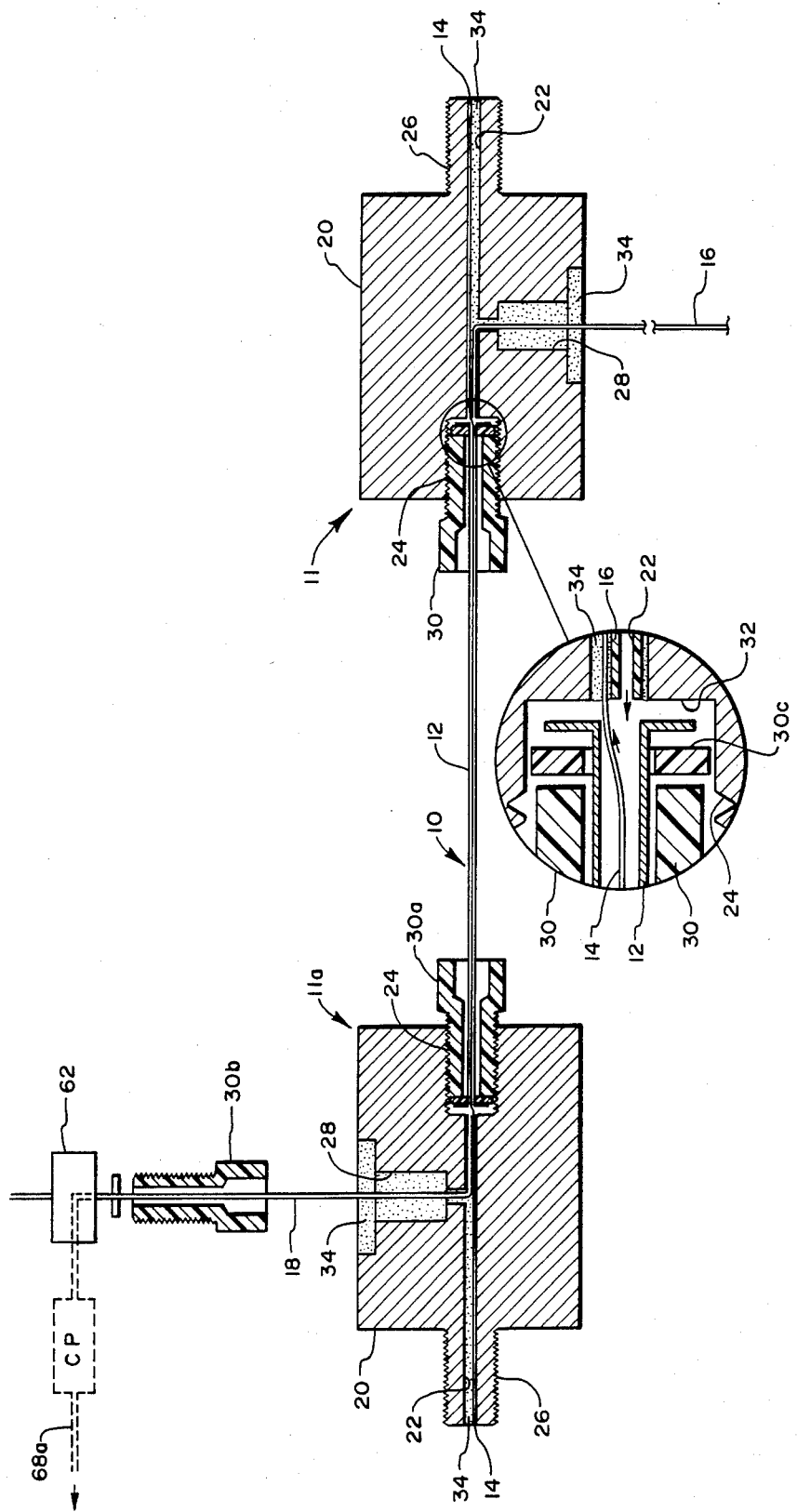
FIG. 1 is a vertical sectional view through the hollow fiber dialytic chamber and associated parts with the sheath, which normally surrounds the column, removed for clarity, details of the assembly being shown on larger scale and expanded in the insert.
Figure 2:
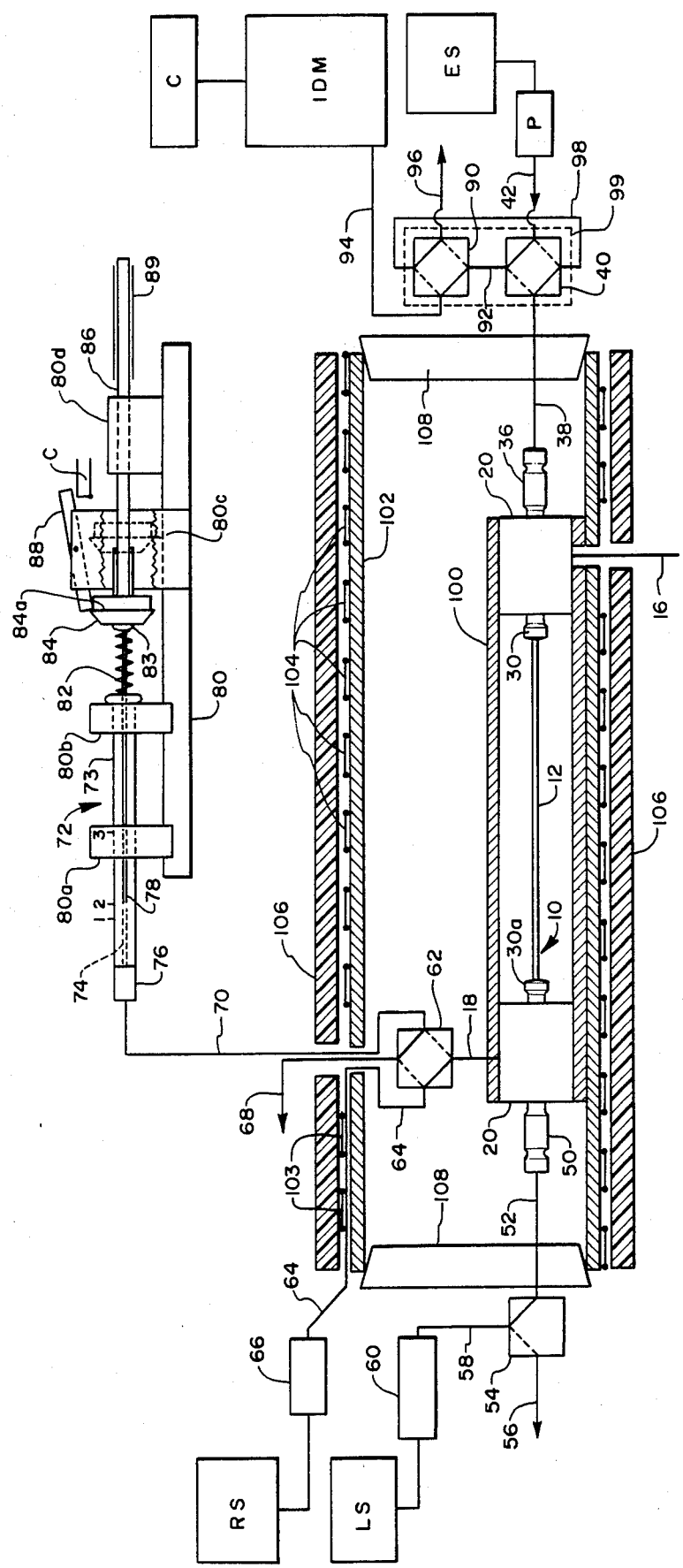
FIG. 2 is a side view, partly in section, of the dialyzing injection system of the invention with valves and pumps shown diagramatically.

The apparatus embodying the invention as illustrated in FIGS. 1 and 2 may be used with any instrumental detection means (IDM) and as a preferred embodiment is particularly described in combination with a modified Dionex Model 10 Ion Chromatograph. This apparatus comprises a dialytic chamber 10 and associated means 11 and 11a, respectively, for holding the chamber 10 in liquid-tight relation to them at its ends, for feeding liquid to it, and for discharging liquid from it. The dialytic chamber 10 comprises a length 12 of tubing, e.g., TFE tubing, about 10 to 18 inches long having an internal diameter (i.d.) of about 0.022 inch, with a strand of hollow fiber dialytic membrane 14 inside it, e.g., Type CIIM Cuprophane dialytic fiber having an i.d. of about 200 $\mu$m, an outside diameter (o.d.) of about 220 $\mu$m, and long enough to extend somewhat beyond the ends of the means 11 and 11a for a purpose to be described. Inlet means 16 is provided in holding and liquid feed means 11 to supply liquids to the inlet end of tubing 12, and outlet means 18 is provided in holding and liquid discharge means 11a to conduct discharge liquid from the other or discharge end of tubing 12.

The structure of means 11 and 11a is identical, each being a Lexan fitting 20 comprising a length of cylindrical stock, e.g., of metal, machinable plastic, and the like, having an axial passageway or bore 22, e.g., about 1/16 inch in internal diameter, a coaxial internally threaded recess 24 at one end, a coaxial externally treaded projection 26 at the opposite end and a radial or transverse bore 28 intersecting passageway 22 outwardly from the end of recess 24. Bore 28 is illustrated as having an i.d. for a short distance near its intersection with passageway 22 approximately equal to the i.d. of passageway 22, then a somewhat larger i.d. for the remaining portion of its length.

An Altex fitting 30 having an external threaded end conforming to the internal thread in recess 24 is screwed into the recess where a liquid tight fit is formed in the manner best seen in the exploded view of the enlargement or insert of the area within the circle of FIG. 1. Inlet means 16 is bent at its inner end toward recess 24 and terminates in the plane of the bottom wall 32 thereof. Its o.d. is sufficiently smaller than the i.d. of passageway 22 that the free end of the hollow fiber dialytic membrane 14 can pass by inlet means 16 between it and the wall of the passageway 22 to the end of projection 26. These parts are held in position by cement 34, preferably black or otherwise colored silicone glue, that is introduced until it fills bore 22 and recess 28. Tubing 12 is passed through fitting 30, a washer 30c and is then flanged over the washer by heat, as shown. Then when fitting 30 is screwed down tight, it forces the flange tightly against wall 32 to form the liquid-tight fit or seal, mentioned above. The free end of the hollow fiber dialytic membrane 14 and the cement 34 are cut off in the plane of the free end of projection 26 so that the passageway through fiber 14 is fully open at the exposed end thereof.

The structure of liquid discharge means 11a is a mirror image of that of liquid inlet means 11, the parts thereof which are the same as described for means 11 bear the same reference numbers except that the Altex fitting in means 11a is numbered 30a, the annular tube is numbered 18 as the outlet end of tubing 12 to distinguish it from the inlet end 16. Fitting 30b on the outer end of tube 18 secures it in liquid-tight relation to a valve to be described later.

Referring now to FIG. 2, an internally threaded fitting 36 having a tube 38 connected at one end thereto, e.g., a 1/16 inch i.d. tubing to match the i.d. of passageway 22, is screwed onto the externally threaded projection 26 of holding and liquid feed means 11. The other end of tube 38 is connected to a valve 40, e.g., an Altex slider valve, connected to an eluent line 42 which receives eluent from an eluent supply ES under pressure produced by a continuously running eluent pump p. Further connections to valve 40 are described hereinafter.

A fitting 50, similar to fitting 36, having a tube 52 connected at one end thereto , e.g., a 1/16 inch i.d. tubing to match the i.d. of passageway 22, is screwed onto the externally threaded projection 26 of holding and liquid discharge means 11a. The other end of tube 52 is connected to a valve 54, e.g., an Altex slider value, connected in one position through a dashed line to a drain line 56 and in another position through a solid line transfer line 58 to a transfer pump 60 which receives liquid from a liquid supply LS.

Outlet tube 18 is connected at its external end to a valve 62, e.g., an Altex slider value, which has three other connections (in the position shown): (a) through a solid passage to a rinse pump line 64 connected, in a manner described hereinafter for thermally equilibrating the rinse solutions, to a rinse pump 66 which receives rinse liquid from a rinse supply RS, (b) through a dashed passage to a drain line 68 for discharging liquid to drain at one stage of the operation of the equipment as described hereafter, and (c) through a dashed line to one end of a syringe pump line 70.

The other end of line 70 connects to a syringe pump 72 which has a body 73 provided with a chamber 74 therein, preferably a cylindrical chamber, closed at one end by an end fitting 76 by means of which line 70 is held in communication with chamber 74. The bore of chamber 74 conforms in internal cross section to the external cross section of piston 78, both preferably being circular so that a liquid tight but slidable connection is formed between them. Support means 80 which supports pump 72 and associated parts comprises a base and a plurality of upright supports 80a, 80b, 80c and 80d. A compression spring 82 surrounds the exposed end of piston 78 between the end of pump body 73 and a head 83 secured to the external end of piston 78. Spring 82 biases head 83 and piston 78 to an extended position of 78 in relation to pump body 73. Movement of head 83 is controlled by pusher means 84 which is mounted on a rod or tube 86 which is reciprocable in support upright 80d. Surrounding the free end of member 86 is a stop member 89 which permits pusher 84 to move the inner end of piston 78 to the left only as far as position 1. A lever 88 pivotally mounted on support upright 80c is adapted to engage a shoulder 84a to hold the inner end of piston 78 at position 2. When the end of lever 88, which engages shoulder 84a, is moved free of the shoulder, spring 82 moves the head 83 and pusher 84 to the right to the dashed line position with the inner end of piston 78 at position 3. The open box C adjacent to lever 88 represents the portion of controller C that operates pump 72 and associated parts as hereinafter described.

A sample injection valve 90 is connected in the position shown for liquid flow: (a) to valve 40 by solid sample supply line 92, (b) to the instrumental detection means (IDM), e,g., separation column of a chromatograph (not shown) by a solid line 94, (c) to a drain (not shown) by a solid sample drain line 96, and (d) to valve 40 by a solid sample loop 98. There is also a mechanical connection represented by dashed line 99 between valve 40 and valve 90. The IDM and syringe pump 72 may be connected to a controller C for fully automated computer control and operation.

A tube 100 surrounds and connects to cylinders 20 to hold means 11 and 11a in spaced position at the ends of tube 12. Tube 12 may be any desired length and shape, e.g., straight (as shown), catenary or coiled (not shown), etc. Tube 100 is secured to the interior wall of a length of pipe 102, e.g., an aluminum pipe, which is surrounded by a thermal equilibration coil in line 64 which is concentric with that portion marked 103 of an electric heating coil 104, both surrounding pipe 102 and being insulated against loss of heat by a layer of insulation 106, preferably a closed cell plastic foam. Each end of pipe 102 is closed by an insulating plug 108, preferably also made of closed cell plastic foam.

Figure 3:
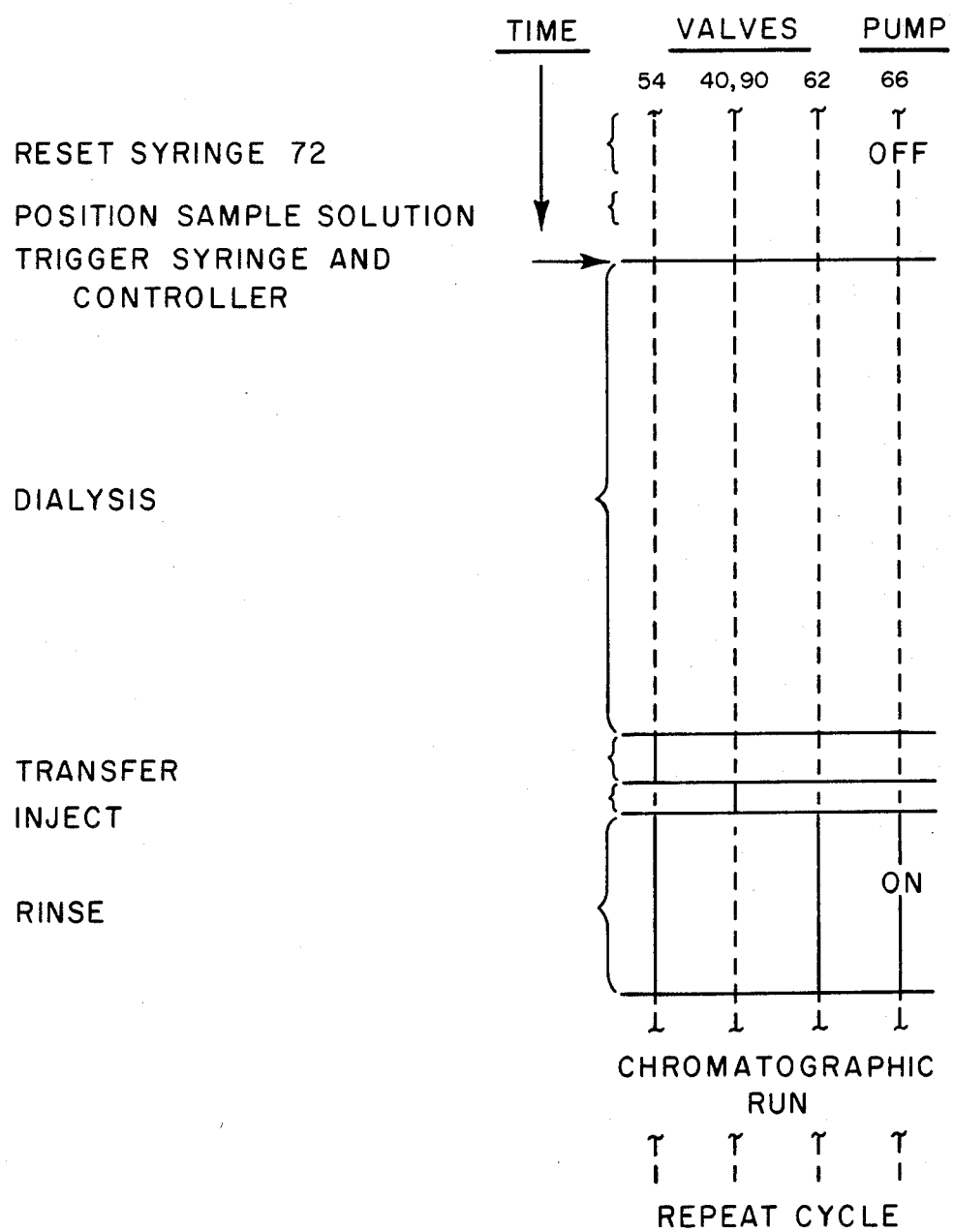
FIG. 3 represents a dialysis injection cycle with its dashed and solid lines corresponding to the dashed and solid lines associated with the valve positions in FIG. 2.

The operation of the apparatus just described in which IDM is a chromatograph may comprise a sequence of steps illustrated in FIG. 3 in which time runs vertically downwardly from the reset position of syringe pump 72, shown in FIG. 2. Pump P runs continuously, Pumps 60, 66 and 72 run intermittently. The dashed and solid lines in FIG. 3 correspond to the dashed and solid lines, respectively, in valves 54, 40 and 90 as a unit, and 62. The apparatus used in Working Example 1 described hereinafter comprises Type CIIM hollow fiber having an i.d. of 200 $\mu$m and and o.d. of 220 $\mu$m which is designed for dialysis of the middle molecular weight range (below about 500-2000 Daltons) Tubing 12 has an i.d. of about 0.022 inches. The annular space in tubing 12 forms a first passageway through the dialytic apparatus for sample liquid while the open channel through the hollow fiber 14 forms a second passageway therethrough for recipient liquid. The wall of tubing 14 constitutes a dialytic membrane separating the first passageway from the second passageway through which materials pass which move from one liquid to the other during dialysis. The liquids are kept in contact with each other through the membrane for a period of time long enough to reach essential equilibrium, preferably by keeping the liquids in nonflowing condition during that time period, although the dialysys goes on if one liquid is, or both liquids are, flowing. Essential equilibrium as defined herein can be achieved with flowing liquids if the passageways are long enough, in relation to the rate of flow of the liquids, to provide a period of contact of the liquid in one passageway with the liquid in the other passageway at least equal to the period of time required to reach essential equilibrium at the flow rate of the liquids in the passageways. Inlet tube 16 has an i.d. of about 0.015 inch and extends about 5 cm from fitting 11, to permit immersion at cyclic times into sample liquid in a beaker or like container. Outlet tube 18 also has an i.d. of about 0.015 inches. The ratio of the annular volume in tubing 12 to the column or the cylindrical volume in 14 is about 87 to 13, i.e., about 13% of the total volume is inside the hollow fiber 14. The liquid sample to fill the annular chamber in tubing 12 and associated parts is supplied by a beaker or other source containing it which is placed over inlet end 16 during the time piston 78 is moved from position 2 to position 3. The atmospheric pressure on the liquid in the beaker forces liquid to flow into part of the cavity formed by 16, 12, 18, 62, 70 and 74 when a decreased pressure in that cavity is created by movement of the piston 78 from position 2 toward position 3.

In assembling the parts of the dialytic chamber, the fiber 14 is strung through the passageways 22 and tube 12 taking care that it pulls freely and is not flattened as it passes by the bent ends of tubes 16 and 18. Excess fiber 14 is temporarily left extending beyond the ends of projections 26 of means 11 and 11a for a reason to be explained hereinafter. Black silicon rubber glue is introduced into each fitting 20 until it is visible at both ends of passageway 22. Care is taken not to seal over the inner ends of the tubes 16 and 18 and to leave a mound of glue at each end surrounding and centering the fiber 14 while leaving the ends thereof open. After about 24 hours of curing the mound of glue and the deliberately left excess hollow fiber mentioned hereinabove at the outer ends of 11 and 11a are trimmed off with a razor blade. Care is taken in applying and tightening fittings 36 and 50 not to damage the open ends of fiber 14. Altex slide valves 54, 40 and 90 as a unit, and 62 have pneumatic actuators (not shown) which are driven by compressed air controlled by solenoids (not shown) which in turn are operated by a programmed digital controller C. The syringe 72 is a 100 $\mu$L Hamilton Gas-Tight syringe also operated by controller C which, when operated as described, measures reproducible sample volumes. Depressing piston 78 to position 1 expels the contents of the cylinder 74 occupied by piston 78 between positions 3 and 1. A 10 $\mu$L bubble of air is introduced by moving piston 78 from position 1 to position 2 at a time when inlet tube 16 is open to the atmosphere and holds it there by lever 88. This air bubble effectively separates liquid in the said cavity from sample liquid next to be introduced into said cavity. A predetermined volume of sample is thereafter introduced into at least part, and preferably all of dialytic chamber 10, which is part of the cavity formed by 16, 12, 18, 62, 70 and 74, as described above by immersing the inlet of tube 16 into sample liquid in a container and triggering the syringe by releasing lever 88 from the stop 84a (may be part of the computer control functions) which allows spring 82 to move piston 78 from position 2 to position 3. Transfer pump 60 is a Model 396 Lab Data Control Instrument Mini-pump which is set at 46 mL/hr. When the dialysis time has elapsed, pump 60 transfers the recipient solution inside fiber 14 through the 7 cm length of tubing 38 to the sample loop 98 of valve unit 40, 90 (about 100 $\mu$L). Injection of the recipient solution is accomplished by valve unit 40, 90 in the eluent stream 94, as indicated. The location of this injection is just ahead of the position of the usual sample injection valve in the sample supply line leading to the ion chromatograph used in the prior art. In other words, the apparatus of FIG. 2 of the invention replaces the same injection port function of the prior art.

Rinse or transfer pump 66 is a peristaltic pump set to deliver 2.5 mL/min. Operation of pump 66 expels the old sample solution and rinses the annular space in tubing 12 with water or other rinse solution. Water or other solution from the liquid supply LS is pumped by pump 60 through fiber 14 at the same time the annular space is rinsed. At the conclusion of the rinse cycle, dialyzable solutes present in the rinse solution will equilibrate with the water or other liquid inside fiber 14 to provide the recipient solution for the next sample. These dialyzable solutes may be omitted from the rinse solution if it is desired to have pure water as the recipient medium.

A 12 inch length of 3.5 inch o.d. (3/16 in wall thickness) aluminum pipe 102 serves as the thermostating vessel for the dialytic chamber. Line 64 between valve 62 and pump 66 includes 24 feet of 0.047 inch i.d. TFE tubing wrapped around pipe 102 to provide for thermal equilibration of the rinse solution. Heat sink compound may be used to improve thermal contact with the TFE tubing. Pipe 102 is further wrapped with aluminum foil on which electric heating coil 104, e.g., a 9 foot, 63 watt heating tape, is wound. Coil 104 is covered by a second layer of aluminum foil and finally by the closed-cell foam insulation 106. Temperature is regulated at 37° C. by a Tronac Model PTC 40 Temperature Controller with a thermistor probe mounted on the outside surface of the aluminum pipe.

The dialysis-injection cycle is shown in FIG. 3 as it is programmed into digital controller C built especially for this purpose. The timing of the dialysis, transfer, injection and rinse portions of the cycle is based on the electrical signal generated by an optical revolution counter attached to the drive shaft of reciprocating transfer pump 60. This pump runs continuously but at various strokes/minute, although water is transferred to tubing 52 by valve 54 only during the transfer and rinse portions of the cycle. All switching occurs while this pump is on the back stroke and the transfer liquid is motionless. Typical numbers of pump strokes, are 100, 5, 3, 30 for dialysis, transfer, injection and rinse respectively. These settings must be optimized for a particular dialyzing injection system. The equilibration and rinse times depend on the length and diameter of the dialytic chamber, whereas the number of transfer strokes depends on the volume of the tubing connecting the dialytic chamber with valve unit 40, 90. The dialysis-injection cycle is triggered simultaneously with release of syringe pump 72 which permits ambient air pressure to force liquid sample into the annular space in tubing 12.

The term "unfilterable material" is used herein to identify material suspended in a liquid which is small enough to pass through filter paper and is therefore not removable by filtration.

The term "essential equilibrium" as used herein means that the dialysis taking place through the dialysis membrane has progressed to the stage where the concentration of the solutes dissolved in the recipient liquid which have passed through the membrane from the sample liquid is near enough to the concentration of these solutes in the sample liquid that the difference has no material effect on the essential features of the process of the invention, e.g., it is at least about 90% of being the same, and preferably is at least about 98% of being the same, and the recipient liquid is essentially free from the interfering material in the same liquid.

WORKING EXAMPLE NO. 1

Forty-eight $\mu L$ of sample is required to just fill the 0.015 inch i.d. needle and a dialytic chamber having a 147 mm length of 0.022 inches i.d. TFE tubing. Repeatability of sampling may be checked using a 0.154 M NaCl solution dialyzing into water. Peak heights are measured without any intervening chromatographic column. With sample volumes of 40, 50 and 60 $\mu L$ the observed average peak heights are $666 \pm 5(8)$, $720 \pm 6(11)$, and $734 \pm 3(4)$ (arbitrary units), respectively, where the errors given are $\pm 1$ standard deviation and the number of peaks averaged are given in parentheses. Results of runs in accordance with this working example indicate that precision is not dependent upon sample size. A distilled water sample immediately following a 0.154 M NaCl sample showed a carryover peak of less than 0.25% of the former peak.

After a dialysis time of 27 seconds (40 pump strokes), dialysis of 0.154 M NaCl into water at 37° C. is 90% of that for complete equilibration i.e., the concentration of NaCL on the recipient liquid side of the dialysis membrane is 90% of the concentration of NaCl on the sample side of the dialysis membrane. If the dialysis time is increased to 54 seconds (80 strokes) dialysis is 98% of equilibration. $Ca(NO_3)_2$ and $Mg(NO_3)_2$ dialyze into recipient water at the same rate as NaCl. However, for dialysis of $Ca^{2+}$ and $Mg^{2+}$ from 0.154 M NaCl into 0.21 M Tris buffer ($[Tris]+[HTris^+]=0.21$ M), 62 seconds (92 strokes) are required for 90% of equilibration and for dialysis into 1.05 M Tris buffer, 135 seconds (200 strokes) are required. Calcium and magnesium ions in protein solutions (human serum) dialyze into 0.21 M Tris buffer at the same rate as they do from 0.154 M NaCl.

Repeatability of measurements with protein containing samples may be checked by thawing and analyzing frozen aliquots of a pooled human serum sample. The peak heights for magnesium and calcium are calibrated against a standard containing 0.154 M NaCl, $0.808 \times 10^{-3}$ $Mg(NO_3)_2$ and $1.73 \times 10^{-3}$ M $Ca(NO_3)_2$. Fifteen measurements of the pooled serum over a two week period give $(0.59 \pm 0.03) \times 10^{-3}$ M $Mg^{2+}$ and $(1.62 \pm 0.07) \times 10^{31\ 3}$ M $Ca^{2+}$. Errors given are $\pm 1$ standard deviation. The relative standard deviations, 5% and 4% respectively, are characteristic of ion chromatographic measurements made by direct injection.

Peak heights are linear with concentration in the range measured, from 0 to $1.7 \times 10^{-3}$ M $Ca^{2+}$, with a relative standard deviation of 3%.

WORKING EXAMPLE NO. 2

A dialytic chamber constructed with a 55 mm length of tubing 12 having an i.d. of 0.038 inches surrounding the hollow fiber 14 for most of its length with Lexan at each end. The hollow fiber volume represents 6% of the total volume in this device and peak heights obtained are proportionately smaller than with the dialytic chamber used in working Example No. 1. A dialysis time of 40 seconds (60 pump strokes) is required for dialysis of 0.154 M NaCl into water at 37° C. to be 90% of equilibration. In all other respects the results of Working Example No. 2 are of the same quality as those of Working Example No. 1.

The dialyzing injection system of the present invention is a substantial improvement over previous methods of sample preparation by dialysis or filtration. The dialyzing time is not lengthy (about 1 minute) and can be overlapped with the elution of the previous sample. There is little loss of precision introduced by the dialysis manipulation. Buffers or background compounds can be added to the material to be injected into the chromatograph simultaneously with the dialytic, if desired, by adding them to the water of the dialysis chamber rinse solution. Analysis of low volume samples is facilitated because a minimum volume of sample is required by this method. The system also lends itself to fully automated sample handling.

Instead of operating the apparatus of FIG. 2 intermittently as described above, it may be operated continuously with much superior results than the prior art and with almost as good results as the preferred intermittent method of operation. The only change in apparatus required is illustrated in dashed lines in FIG. 1 in which a continuous pump CP (FIG. 1) is used instead of intermittent pump 72 and valve 62 is locked in the position where line 18 is connected to a drain line 68a. The same results could be obtained by providing a connection to drain in 11a exactly like the inlet line 16 in 11 with a continuous pump between 11a and drain.

Other means of instrumental detection which may be used in the invention instead of the Dionex Chromatograph referred to above include Series 1 Perkins-Elmer liquid chromatograph, Model 554 Perkins-Elmer spectrophotometer, Model 650-10 Perkins-Elmer fluorescence spectrophotometer, and Sargent-Welch Model 4001 polarograph.

Although the invention has been described and illustrated with reference to specific apparatus and process steps, those skilled in the art will recognize and appreciate that modifications and variations may be made in apparatus and process without departing from the principle of the invention disclosed or from the scope of the invention as defined in the following claims.

Having thus described and illustrated the invention, what is claimed is:

1. A method of analyzing a liquid sample by instrumental detection which comprises subjecting the sample to be analyzed, which contains undesired, unfilterable material that would interfere with the instrumental detection, to equilibrium dialysis through a cylindrical dialysis membrane from a first capillary passageway which receives the liquid sample into a second capillary passageway which receives the recipient liquid to form a liquid analyte containing that portion of the sample which passes through the dialysis membrane from the liquid containing the sample into the recipient liquid, said analyte being essentially free of such interfering material, and flowing said analyte into the instrument to subject said analyte to instrumental detection.

2. A method as set forth in claim 1 in which the volume of recipient liquid subjected to instrumental detection is up to about 1 mL.

3. A method as set forth in claim 1 in which the dialytic membrane is rinsed with rinsing liquid after flowing each batch of recipient liquid into the instrument.

4. A method as set forth in claim 1 in which the flow of liquid into the first capillary passageway surrounding the dialytic membrane is carried out by ambient air pressure on the surface of a body of sample liquid upon reduction of pressure at the trailing end of said membrane.

5. A method as set forth in claim 4 in which an air bubble is produced in the stream of liquid in the first capillary passageway surrounding said membrane just in advance of the influx of sample liquid into it.

6. A method as set forth in claim 5 which comprises completely automating said operations.

7. A method of analyzing chromatographically a liquid sample which comprises subjecting the liquid sample to be analyzed, which contains undesired, unfilterable material that would interfere with the chromatographic analysis, to dialysis through a dialytic membrane as a non-flowing liquid annulus containing the sample surrounding a non-flowing column of recipient liquid less than about 1 mm in diameter, in which the ratio of the volume of sample-containing liquid in the annulus to the volume of recipient liquid in the column is at least 1:1, until essential equilibrium is reached, and then subjecting the recipient liquid containing the portion of the sample that has passed through the membrane to chromatographic analysis.

8. A method of analyzing chromatographically a liquid analyte which comprises subjecting a liquid sample to be analyzed, which contains undesired, unfilterable material which would interfere with the chromatographic analysis, to dialysis by flowing (a) recipient liquid into a column about 200 $\mu$m in diameter, and (b) liquid sample into an annulus surrounding and separated from the recipient liquid in the column by a dialytic membrane, and allowing the liquids to reach essential equilibrium, then flowing the recipient liquid as the analyte into liquid chromatographic analysis means.

9. Apparatus for analyzing a liquid sample by instrumental detection comprising an elongated cylindrical column constituting a second capillary passageway formed by a dialyzing membrane adapted to receive recipient liquid; a surrounding annular chamber constituting a first capillary passageway; means adapted for flowing into the cylindrical chamber a column of recipient liquid; means adapted for flowing from a removable container a sample liquid containing undesired unfilterable material that would interfere with instrumental detection into the annular chamber; means for maintaining contact of said liquids through said membrane for a predetermined time long enough for the liquids to reach essential equilibrium by transporting a substantial portion of dialyzable liquid through said membrane from the sample liquid essentially free from said interfering material to the recipient liquid and to form a recipient liquid containing dialyzed sample material as an analyte; and means for flowing recipient liquid containing the analyte into instrumental detection means.

10. Apparatus as set forth in claim 9 in which the means for flowing sample liquid into the passageway adapted to receive it is a syringe pump.

11. Apparatus as set forth in claim 9 in which said instrumental detection means is a chromatograph.

12. Apparatus as set forth in claim 9 in which said instrumental detection means is a spectrophotometer.

13. Apparatus as set forth in claim 9 in which said instrumental detection means is a fluorimeter.

14. Apparatus as set forth in claim 9 in which said instrumental detection means is an electrometric determinator.

15. Apparatus as set forth in claim 9 in which said means for establishing said essential equilibrium maintains the liquids in non-flowing condition in contact with said membrane during said period of time.

16. Apparatus as set forth in claim 9 in which said means for establishing said essential equilibrium maintains the liquids in flowing condition in contact with said membrane during said period of time.

17. Apparatus as set forth in claim 9 which further comprises means for regulating the temperature of liquids in said passageways during said period of time.

18. Apparatus as set forth in claim 9 which further comprises means for completely automating all said means.

* * * * *